United States Patent [19]
Fowler et al.

[11] Patent Number: 5,752,918
[45] Date of Patent: May 19, 1998

[54] MODULAR MEDICAL PRESSURE TRANSDUCER

[75] Inventors: James H. Fowler, Hilliard; Charles R. Patzer, Ashville; Warren B. Nicholson, Dublin; Wendell Thompson, Dublin; Glenn D. Brunner, Dublin; Theodore R. Adams, Amlin; Nilesh M. Shah, Columbus, all of Ohio

[73] Assignee: Medex, Inc., Hilliard, Ohio

[21] Appl. No.: 496,080

[22] Filed: Jun. 28, 1995

Related U.S. Application Data

[60] Continuation-in-part of Ser. No. 407,903, Mar. 21, 1995, abandoned, which is a division of Ser. No. 85,352, Jun. 30, 1993, Pat. No. 5,417,395.

[51] Int. Cl.$^6$ .................................................. A61B 5/00
[52] U.S. Cl. ..................... 600/488; 600/486; 600/561; 73/706; 73/721
[58] Field of Search ......................... 73/756, 715, 721, 73/726, 727; 118/612–5, 748

[56] References Cited

U.S. PATENT DOCUMENTS

| | | |
|---|---|---|
| Re. 33,360 | 10/1990 | Reynolds et al. . |
| Re. 33,518 | 1/1991 | McCord et al. . |
| 190,651 | 5/1877 | Webster . |
| D. 283,441 | 4/1986 | Vcelva et al. . |
| D. 302,465 | 7/1989 | Stephens . |
| 344,312 | 6/1886 | Guillemin . |
| 944,312 | 12/1909 | Brede . |
| 1,286,819 | 12/1918 | Snyder . |
| 1,325,902 | 12/1919 | Novick . |
| 2,169,371 | 9/1939 | Payne . |
| 2,371,433 | 3/1945 | Davis . |
| 2,667,184 | 1/1954 | Hailer et al. . |
| 2,762,595 | 9/1956 | Jenne . |
| 3,081,023 | 3/1963 | Taylor . |
| 3,249,105 | 5/1966 | Polanyi . |
| 3,269,550 | 8/1966 | Marcus . |
| 3,429,450 | 2/1969 | Lambert . |
| 3,452,954 | 7/1969 | Lucietto et al. . |
| 3,499,434 | 3/1970 | Ullrich et al. . |
| 3,526,040 | 9/1970 | Young . |

(List continued on next page.)

FOREIGN PATENT DOCUMENTS

| | | |
|---|---|---|
| 0077151 | 9/1982 | European Pat. Off. . |
| 0208955 | 6/1986 | European Pat. Off. . |
| 0201207 | 11/1986 | European Pat. Off. . |
| 0247543 | 5/1987 | European Pat. Off. . |
| 1049697 | 1/1952 | France . |
| 1467702 | 2/1966 | France . |
| 2287827 | of 1976 | France . |
| 2619151 | 4/1977 | Germany . |
| 2156081 | 10/1985 | United Kingdom . |
| 2182247 | 5/1987 | United Kingdom . |
| WO 8602246 | 4/1986 | WIPO . |
| WO9405576 | 5/1991 | WIPO . |
| WO9207396 | 4/1992 | WIPO . |
| WO9310835 | 6/1993 | WIPO . |
| WO9319318 | 9/1993 | WIPO . |

*Primary Examiner*—Robert L. Nasser
*Attorney, Agent, or Firm*—Wood, Herron & Evans, L.L.P.

[57] ABSTRACT

A medical pressure transducer includes a reusable component with channels to either side of a reusable diaphragm, and a disposable dome with mounting wings to either side of a disposable diaphragm and slidably receivable in the channels to mount the dome with the diaphragms in confronting relationship. Camming ramps are provided in the channels and on the wings by which to drive the dome diaphragm into the reusable diaphragm. Where the channels are defined behind outer front walls, the outer surface of one is provided with a tab-receiving slot to receive a locking tab associated with dome to lock diaphragms into confronting relationship. The dome includes second wings spaced from the mounting wings to receive the outer front walls. The second wings have finger gripping portions one of which is a locking paddle supporting the lock tab. In alternative embodiments, the dome wings are edges, fixed or resilient, receivable through slots formed in the reusable component.

92 Claims, 7 Drawing Sheets

U.S. PATENT DOCUMENTS

| | | |
|---|---|---|
| 3,581,929 | 6/1971 | Guenard . |
| 3,587,322 | 6/1971 | Lebdell et al. . |
| 3,592,187 | 7/1971 | Youdin et al. . |
| 3,599,828 | 8/1971 | Conway et al. . |
| 3,628,526 | 12/1971 | Bigliano . |
| 3,631,850 | 1/1972 | Levasseur . |
| 3,646,495 | 2/1972 | Cowmeadow . |
| 3,724,274 | 4/1973 | Millar . |
| 3,818,765 | 6/1974 | Eriksen . |
| 3,855,439 | 12/1974 | Hermann . |
| 3,865,100 | 2/1975 | Kanai et al. . |
| 3,880,151 | 4/1975 | Nilsson et al. . |
| 3,888,559 | 6/1975 | Geib . |
| 3,901,538 | 8/1975 | Blakely . |
| 3,924,881 | 12/1975 | O'Connor . |
| 4,034,612 | 7/1977 | Buckwitz . |
| 4,049,126 | 9/1977 | Halverson . |
| 4,063,553 | 12/1977 | Karsh . |
| 4,064,550 | 12/1977 | Dias et al. . |
| 4,065,970 | 1/1978 | Wilner . |
| 4,072,056 | 2/1978 | Lee . |
| 4,093,076 | 6/1978 | Newton . |
| 4,099,626 | 7/1978 | Magnussen, Jr. . |
| 4,108,008 | 8/1978 | Jowett et al. . |
| 4,113,217 | 9/1978 | O'Connell . |
| 4,168,875 | 9/1979 | Leonard, Jr. et al. . |
| 4,182,367 | 1/1980 | Day . |
| 4,185,641 | 1/1980 | Minior et al. . |
| 4,223,921 | 9/1980 | Goyne et al. . |
| 4,226,124 | 10/1980 | Kersten . |
| 4,227,418 | 10/1980 | Bonner et al. . |
| 4,227,420 | 10/1980 | Lamadrid . |
| 4,252,126 | 2/1981 | Mandl . |
| 4,252,131 | 2/1981 | Hon et al. . |
| 4,279,355 | 7/1981 | Schwartz et al. . |
| 4,291,701 | 9/1981 | Bowman . |
| 4,314,480 | 2/1982 | Becker . |
| 4,325,260 | 4/1982 | Takahashi et al. . |
| 4,348,899 | 9/1982 | Muller . |
| 4,365,635 | 12/1982 | Bowman . |
| 4,398,542 | 8/1983 | Cunningham et al. . |
| 4,410,095 | 10/1983 | Dembicks . |
| 4,416,040 | 11/1983 | Towsley . |
| 4,422,794 | 12/1983 | Deken . |
| 4,462,409 | 7/1984 | Pace et al. . |
| 4,491,015 | 1/1985 | Allemano . |
| 4,499,903 | 2/1985 | Furst et al. . |
| 4,505,157 | 3/1985 | Hong Le . |
| 4,524,938 | 6/1985 | Strahs et al. . |
| 4,535,635 | 8/1985 | Claren et al. . |
| 4,539,849 | 9/1985 | Pike . |
| 4,554,927 | 11/1985 | Fussell . |
| 4,562,845 | 1/1986 | Furst et al. . |
| 4,566,597 | 1/1986 | Caputo et al. . |
| 4,574,811 | 3/1986 | Stephens . |
| 4,589,287 | 5/1986 | Dickens . |
| 4,597,291 | 7/1986 | Motomiya . |
| 4,610,256 | 9/1986 | Wallace . |
| 4,611,822 | 9/1986 | Berhardson . |
| 4,619,431 | 10/1986 | Matsui . |
| 4,686,764 | 8/1987 | Adams et al. . |
| 4,688,864 | 8/1987 | Sorel . |
| 4,691,573 | 9/1987 | Varnum et al. . |
| 4,717,195 | 1/1988 | Okuyama et al. . |
| 4,732,042 | 3/1988 | Adams . |
| 4,770,297 | 9/1988 | Chang . |
| 4,772,217 | 9/1988 | Petersen . |
| 4,776,343 | 10/1988 | Hubbard et al. . |
| 4,779,625 | 10/1988 | Cole . |
| 4,795,440 | 1/1989 | Young et al. . |
| 4,838,865 | 6/1989 | Flank et al. . |
| 4,856,340 | 8/1989 | Garrison . |
| 4,856,658 | 8/1989 | Novak . |
| 4,881,413 | 11/1989 | Georgi et al. . |
| 4,920,972 | 5/1990 | Frank et al. . |
| 4,944,693 | 7/1990 | Puerner . |
| 4,970,900 | 11/1990 | Shepherd et al. ............... 73/756 |
| 4,987,661 | 1/1991 | Kasai . |
| 4,993,265 | 2/1991 | Koen et al. . |
| 5,016,312 | 5/1991 | Frimely . |
| 5,029,478 | 7/1991 | Wamstad . |
| 5,046,625 | 9/1991 | Rushing . |
| 5,112,019 | 5/1992 | Metezler . |
| 5,146,782 | 9/1992 | Rasmussen . |
| 5,155,663 | 10/1992 | Harase . |
| 5,212,989 | 5/1993 | Kodoma et al. . |
| 5,218,972 | 6/1993 | Gorsuch et al. . |
| 5,222,946 | 6/1993 | Kamen . |
| 5,257,547 | 11/1993 | Boyer . |
| 5,257,630 | 11/1993 | Broitman et al. . |
| 5,275,367 | 1/1994 | Frye . |
| 5,279,308 | 1/1994 | DiSabito et al. . |
| 5,322,253 | 6/1994 | Stevens . |
| 5,333,507 | 8/1994 | Vogler et al. . |
| 5,351,548 | 10/1994 | Briggs et al. . |
| 5,392,653 | 2/1995 | Zanger et al. . |
| 5,404,756 | 4/1995 | Briggs et al. . |
| 5,406,952 | 4/1995 | Barnes et al. . |
| 5,410,916 | 5/1995 | Cook . |
| 5,417,395 | 5/1995 | Fowler et al. . |
| 5,551,300 | 9/1996 | Vurek et al. . |
| 5,554,113 | 9/1996 | Novak et al. . |

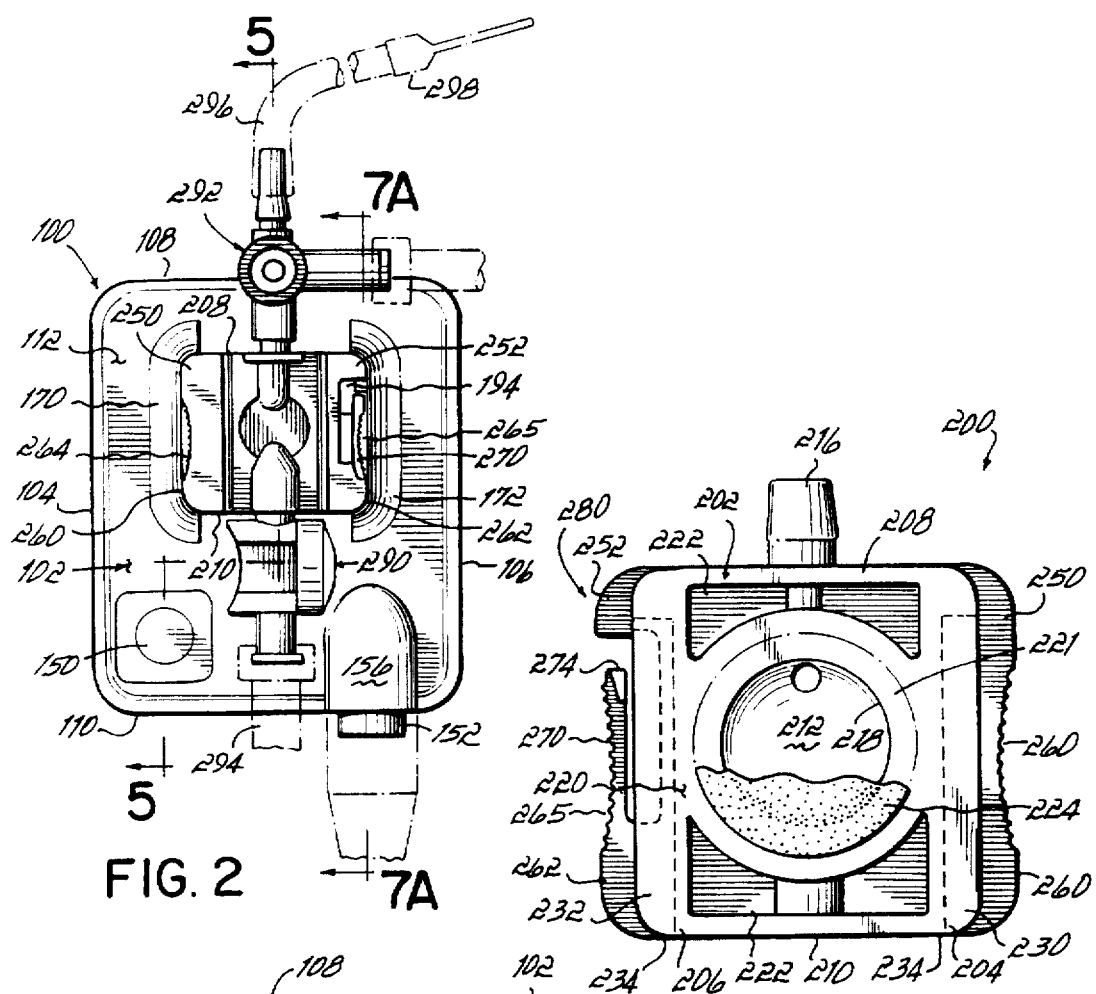
FIG. 2
FIG. 6
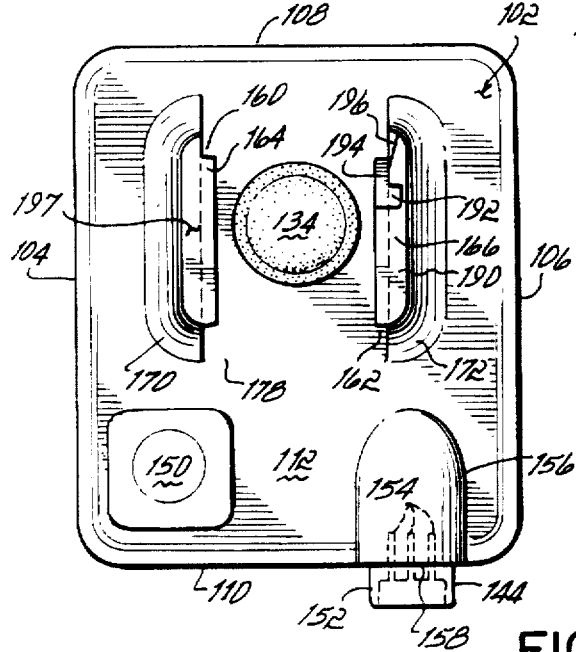
FIG. 3

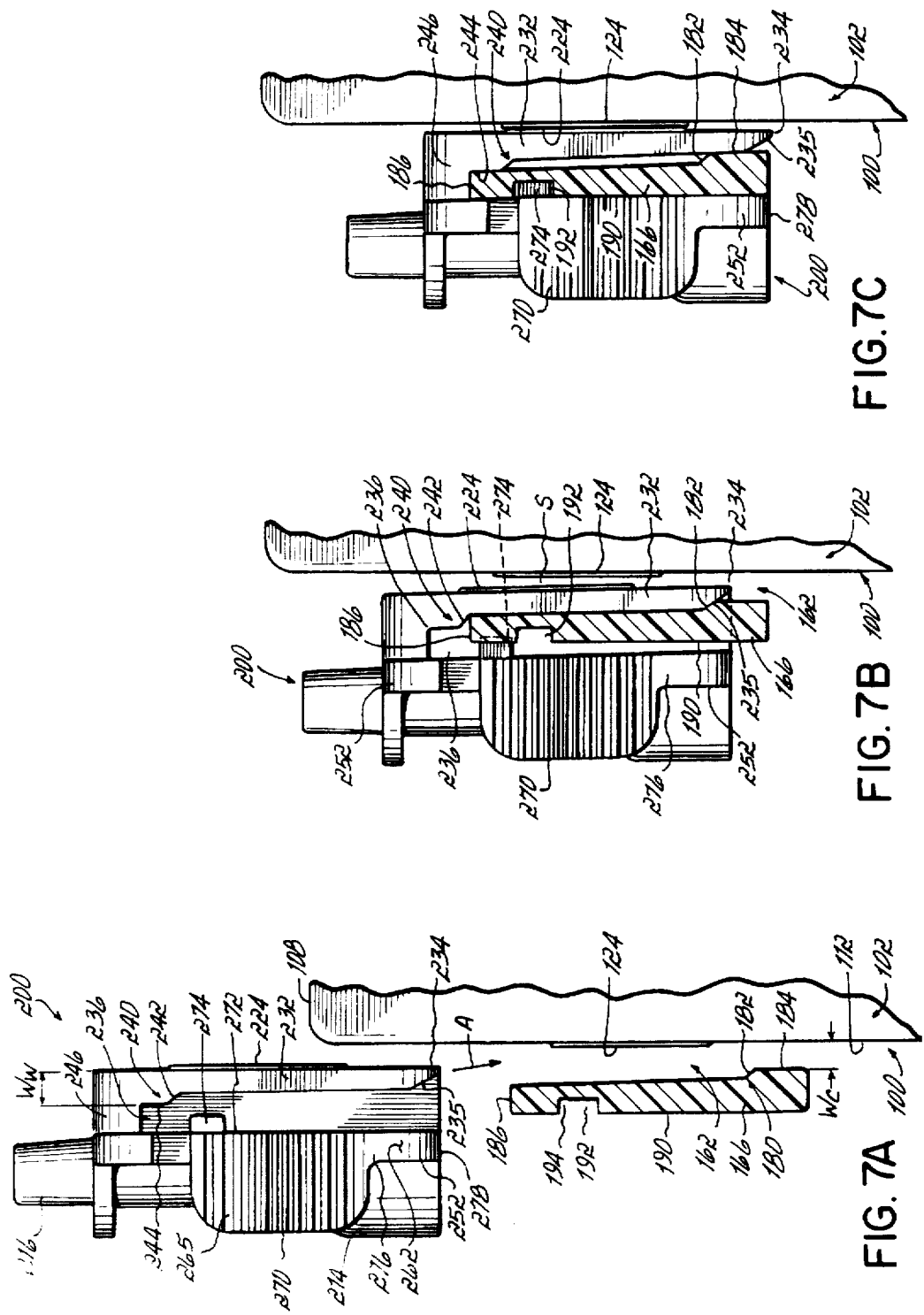

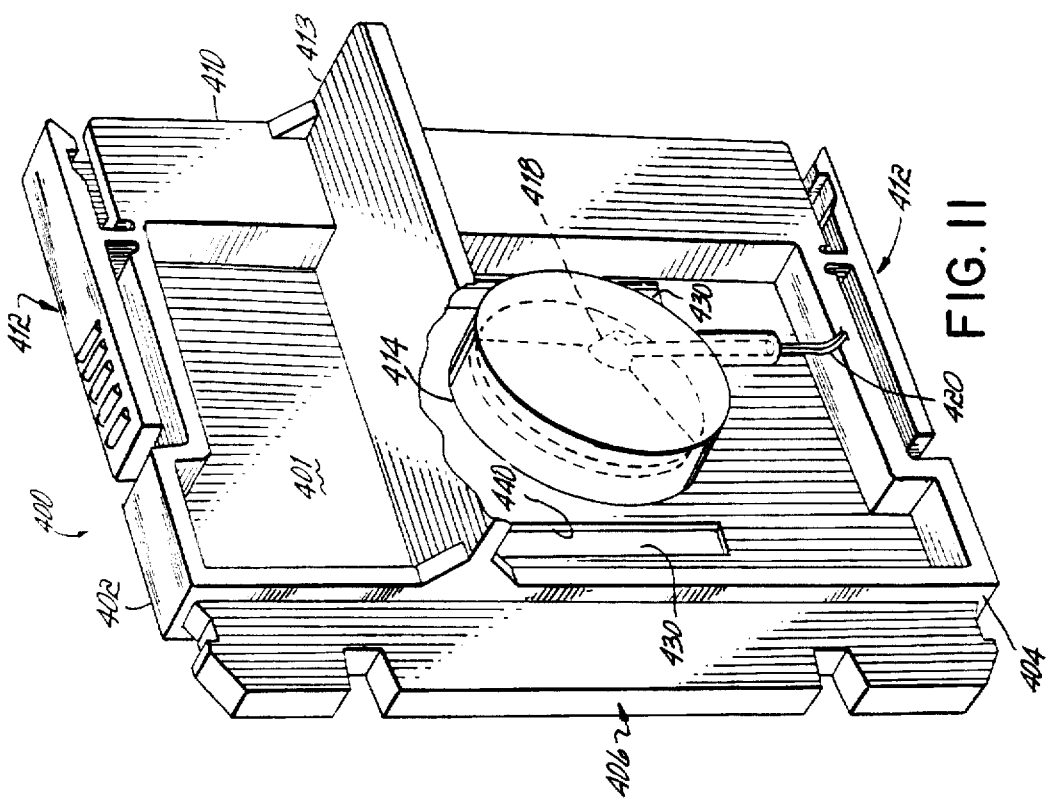
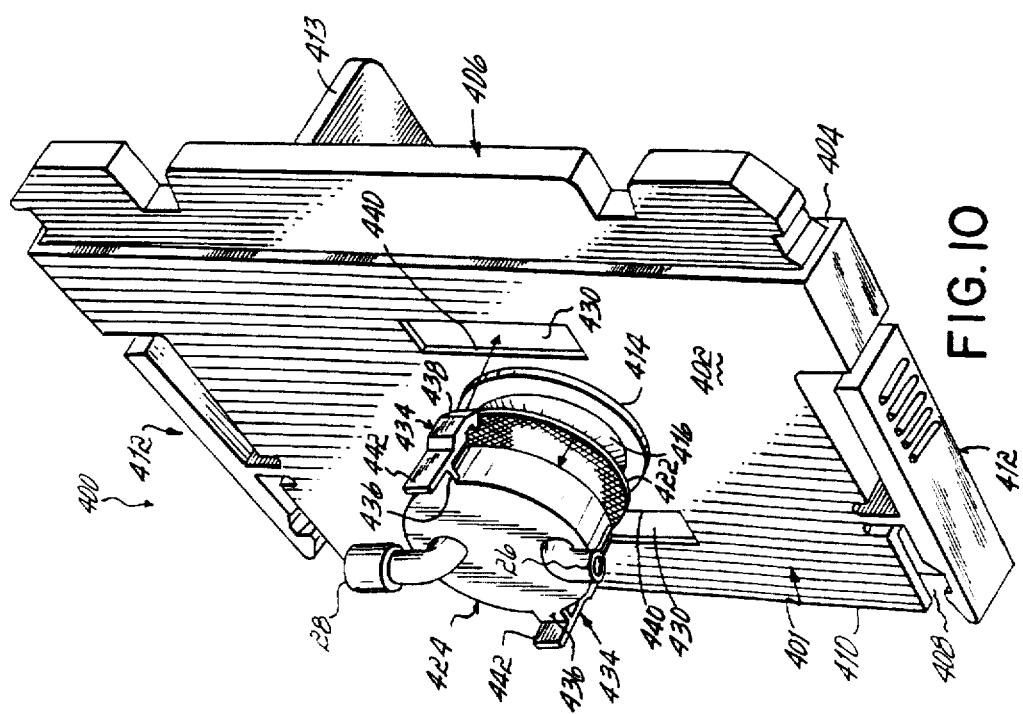

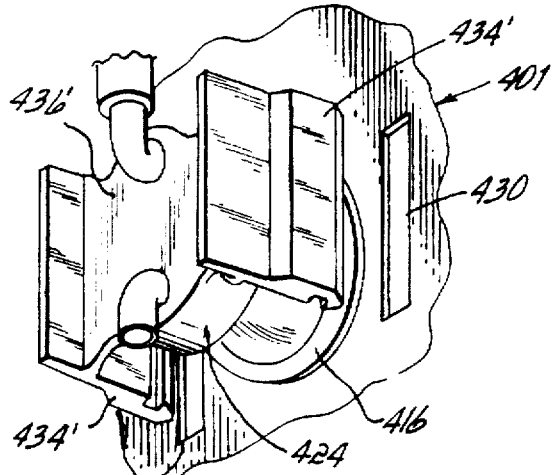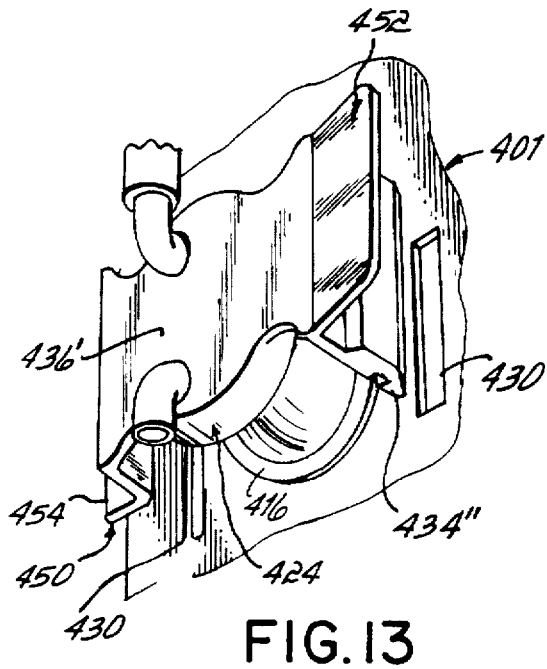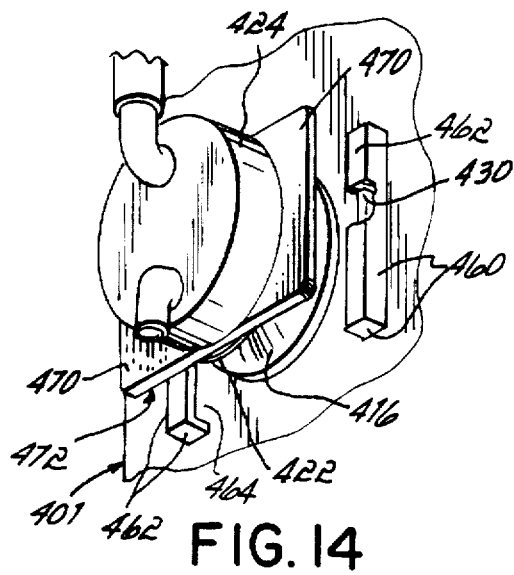

MODULAR MEDICAL PRESSURE TRANSDUCER

RELATED APPLICATIONS

This application is a continuation-in-part of application Ser. No. 08/407,903, filed Mar. 21, 1995, entitled Modular Interconnecting Component Support Plate now abandoned, which is a divisional of application Ser. No. 08/085,352, filed Jun. 30, 1993, now U.S. Pat. No. 5,417,395. The disclosures of aforementioned applications Ser. Nos. 08/407, 903 and 08/085,352 are incorporated herein by reference in their entirety.

BACKGROUND OF THE INVENTION

I. Field of the Invention

This invention relates to medical pressure transducers, and more particularly, to such transducers in which a disposable fluid path component such as a dome is selectively attachable to a reusable sensor component with respective fluid pressure communicating diaphragms of the components in confronting, pressure communicating relationship.

II. Description of Prior Art

In hospital environments, for example, many procedures involve monitoring bodily fluid pressures such as blood pressure. Typically, such pressure is monitored with a medical pressure transducer outside the patient's body and coupled hydraulically to the patient's circulatory system, by way of example, via a catheter introduced into the body. The catheter is coupled via a tube to a fluid path inside the transducer and the tube is filled with saline to hydraulically communicate pressure within the patient's body to the transducer.

The transducer includes a sensor in pressure communication with the fluid path by which to convert the pressure therein to electrical signals corresponding to the pressure. The electrical signals are coupled via a cable to a monitor which provides a visual display of the pressure.

One particularly successful form of such a transducer is provided by a two-component system in which one component with the expensive sensor is reusable, and the other component with the patient-contacting fluid path is disposable. Each component is provided with a diaphragm closing off access to the sensor or the fluid path, respectively. To measure pressure in the fluid path, the disposable component is screwed onto the reusable component with the diaphragms in confronting, pressure communicating relationship to thereby communicate pressure from the fluid path to the sensor. After use, the disposable component is unscrewed from the reusable part and discarded, and replaced with a new, sterile unit.

U.S. Pat. No. 4,920,972, the disclosure of which is incorporated herein by reference, shows an example of a two-component transducer in which the disposable fluid path component, referred to as a fluid dome, is rotatably coupled to the reusable sensor portion. The components are secured together by threaded interaction to bring the diaphragms into confronting, pressure communication relationship. Pressure from the fluid path in the dome is thus communicated through the dome diaphragm and reusable diaphragm and through a cured gel to the sensor of the reusable component. The screwed-together components may then be mounted to an additional part such as a supporting plate which is attachable to a pole as is conventional.

While there has been success with such screw-on types of transducers, the exterior part and the extra manipulation of the support plate is disadvantageous. Moreover, it has been desired to reduce the manipulation required to mount and dismount the dome from the sensor.

SUMMARY OF THE INVENTION

The present invention provides a two-component type of system in which the extra part and manipulation of a supporting plate is eliminated by combining the reusable sensor component as part of the supporting plate. To this end, and in accordance with the principles of the present invention, the reusable component includes the support plate with a sensor permanently associated with the support and the reusable diaphragm in pressure communication with the sensor.

The present invention further provides a disposable dome and reusable sensor system in which the dome is received into engagement with the sensor with less manipulation or dexterity than was required in prior systems. To this end, and in accordance with the principles of the present invention, to facilitate attachment of the dome to the reusable component, the dome is provided with a pair of edges disposed to different sides of the dome and the reusable component is provided with a pair of channel members to different sides of the reusable diaphragm and configured matingly to receive the dome edges such that the diaphragms are brought into confronting relationship by cooperation of the edges and channel members.

In accordance with one aspect of the present invention, the channel members on the reusable component may be a pair of elongated slots through which to receive the dome edges. In this regard, the dome edges may be pivotally mounted arms which releasably lock the dome to the support as they pass into and through the slots. Alternatively, the domes edges may be a fixed L-shaped foot on one side of the dome and a flexible latching arm on the other which cooperate to releasably attach the dome to the reusable component. In a preferred embodiment, the channel members of the reusable component are channels defined behind respective outer front walls, and the dome edges are defined by mounting wings extending outwardly, and preferably in a common plane, to opposite sides of the dome diaphragm to be slidably received into the channels and behind the outer front walls of the reusable component to easily and quickly slide the dome diaphragm into confronting relationship with the reusable diaphragm with very little manipulation or dexterity required by the user. In either event, the reusable component may be formed as the pole-mountable supporting plate thus eliminating that extra part and the extra manipulation thereof otherwise required by the user.

Where the dome is slidably receivable into the reusable component, the confronting, pressure-transmitting relationship of the diaphragms may be enhanced by camming structure associated with either the channel(s) and/or the wing(s) by which to drive the disposable diaphragm into the reusable diaphragm as the dome wings are slidably received into the channels.

Provision of the camming structure allows the two diaphragms to initially be slightly spaced apart, or loosely contacting, through at least part of the travel of the dome into the reusable component. In this way, the diaphragms are not significantly damaged or chafed as they slide by one another. Yet, the camming structure brings the diaphragms into abutting relationship, at least at the end of the travel of the components, such that proper pressure communication is established therebetween. The camming structure may be provided by one or more camming ramps at the terminal end of the sliding travel of the components. One such ramp may be formed as a step at the bottom end of each channel that is last contacted by the dome wing as it reaches the end of its travel. Another such ramp may be formed on each mounting wing at the top end that is last contacted by the outer front wall of the reusable component as the wing reaches the end of its travel.

In accordance with yet a further feature of the present invention, a tab-receiving slot is formed in the reusable component and a locking tab is associated with the disposable dome (or vice versa), the tab and slot engaging together to lock the dome to the reusable component as the dome wings are slidingly received into the channels. The slot is advantageously formed into the outer front wall and the locking tab is elevated above the associated wing on the dome so as to fit into the slot when the diaphragms are in confronting relationship. As a consequence, the dome and reusable components are reliably locked together as if they had been screwed together but without the same dexterity of manipulation required.

In accordance with a still further feature of the present invention, a pair of second wings is provided on the dome spaced above respective ones of the mounting wings to define wall-receiving spaces for the channel-defining outer front walls. Each mounting and second wing pair may each be viewed as providing attachment structure in the form of a channel in the wall-receiving space, and each outer front wall of the reusable component may be viewed as wing-like attachment structure to slide into the wall-receiving channels of the dome. In the preferred embodiment, the second wings overlie and generally conceal the outer walls that define the channels. As a consequence, the assembled transducer does not have the appearance of being in two parts, but instead appears as a solid unit. The overlying relationship between the outer walls and second wings may also provide protection against contaminants entering and fouling the channel.

The lateral side edges of the second wings are advantageously indented and textured (such as by grooving, serrating or knurling) to provide finger-gripping portions by which the operator may manipulate the dome to slide it into and out of the channels. One of the indentations may be simulated with a similarly shaped and textured paddle to carry the locking tab. As a consequence, gripping the second wings serves also to compress the paddle thereby disengaging the tab from the slot and allowing sliding removal of the dome from the reusable component.

By virtue of the foregoing, there is thus provided a medical pressure transducer which eliminates the added part and manipulation of a separate support plate and further provides such a transducer in which the disposable fluid dome is easily mountable and removable from the reusable sensor component. In a preferred embodiment, there is an enhanced pressure transmitting relationship between the diaphragms and with improvements to facilitate operator use of the transducer.

These and other objects and advantages of the present invention shall become apparent from the accompanying drawings and the detailed descriptions thereof.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the principles of the invention.

FIG. 2 is a front view of the transducer shown in FIG. 1;

FIG. 3 is a front view of the reusable component of FIG. 1;

FIG. 6 is a rear, partially cut-away view of the disposable component of FIG. 1;

FIGS. 7A–7C are diagrammatic side views, taken along lines 7A—7A of FIG. 2, to illustrate interaction of the dome wings and reusable component channels;

FIG. 10 is a front perspective view of an alternative embodiment of a transducer in accordance with the principles of the present invention;

FIG. 11 is a rear perspective view of the support plate of the transducer of FIG. 10;

FIG. 12 is a partial, perspective view of a second alternative embodiment of a transducer in accordance with the principles of the present invention;

FIG. 13 is a partial, perspective view of a third alternative embodiment of a transducer in accordance with the principles of the present invention; and FIG. 14 is a partial, perspective view of a fourth alternative embodiment of a transducer in accordance with the principles of the present invention.

DETAILED DESCRIPTION OF THE DRAWINGS

Figure 1:
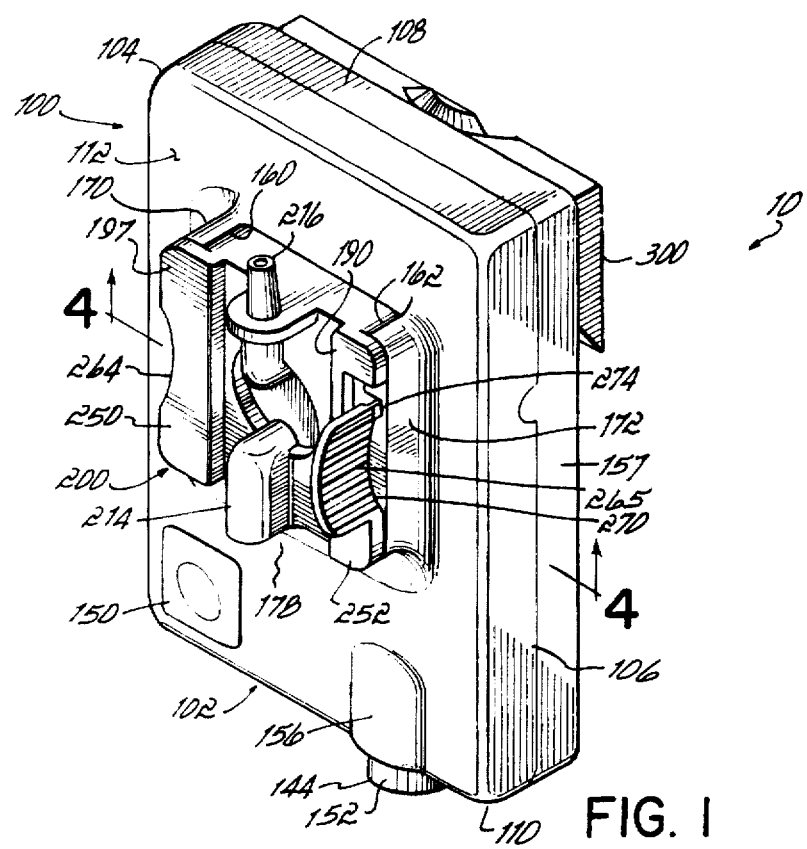
FIG. 1 is a perspective view of a preferred embodiment of a transducer of the invention.

With reference to FIG. 1, there is shown a perspective view of a medical pressure transducer 10 of the present invention. Transducer 10 includes two major components, one being a reusable sensor component 100 of the invention and the other being a disposable fluid dome component 200 of the invention, removably and slidably mounted to reusable component 100.

With further reference to FIGS. 1–5, reusable component 100 is a pole-mountable supporting plate or housing with a reusable pressure sensor system built into it as will be described. To this end, component 100 may be seen as having an opaque plastic support 102 in the form of a plate. Plate 102 has generally planar left edge 104, generally planar right edge 106, and generally planar top and bottom edges 108,110 to define a generally rectangular shape to plate 102. Extending between edges 104,106,108,110 is a generally planar front face 112.

Figure 4:
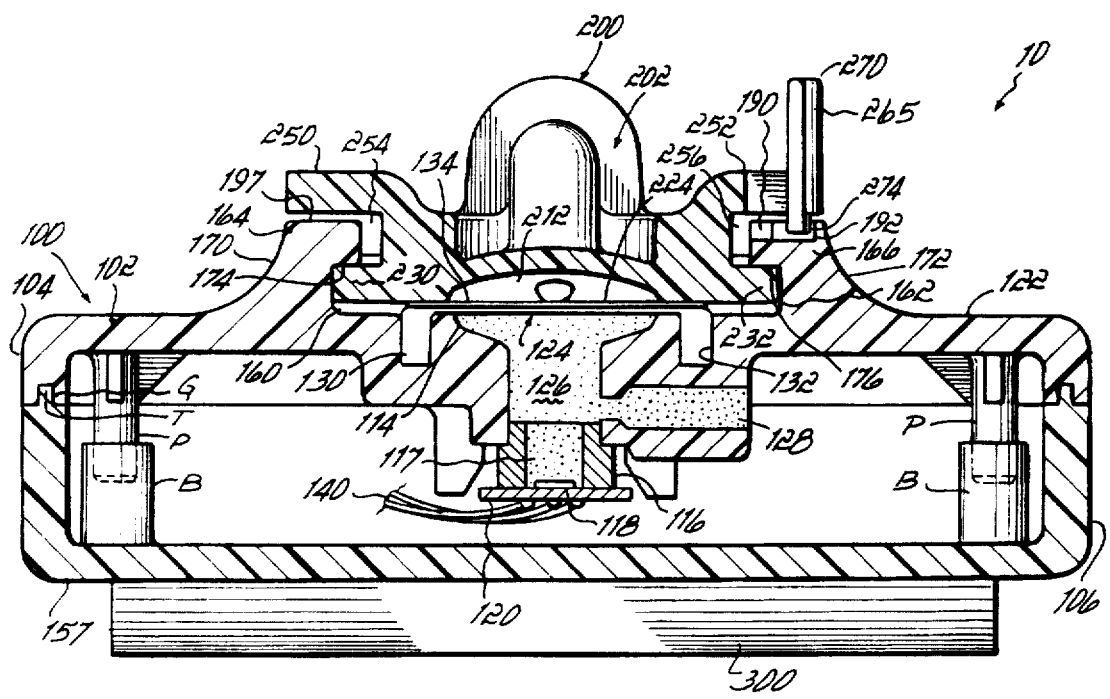
FIG. 4 is a cross-sectional view taken along lines 4—4 of FIG. 1.
Figures 5, 9:
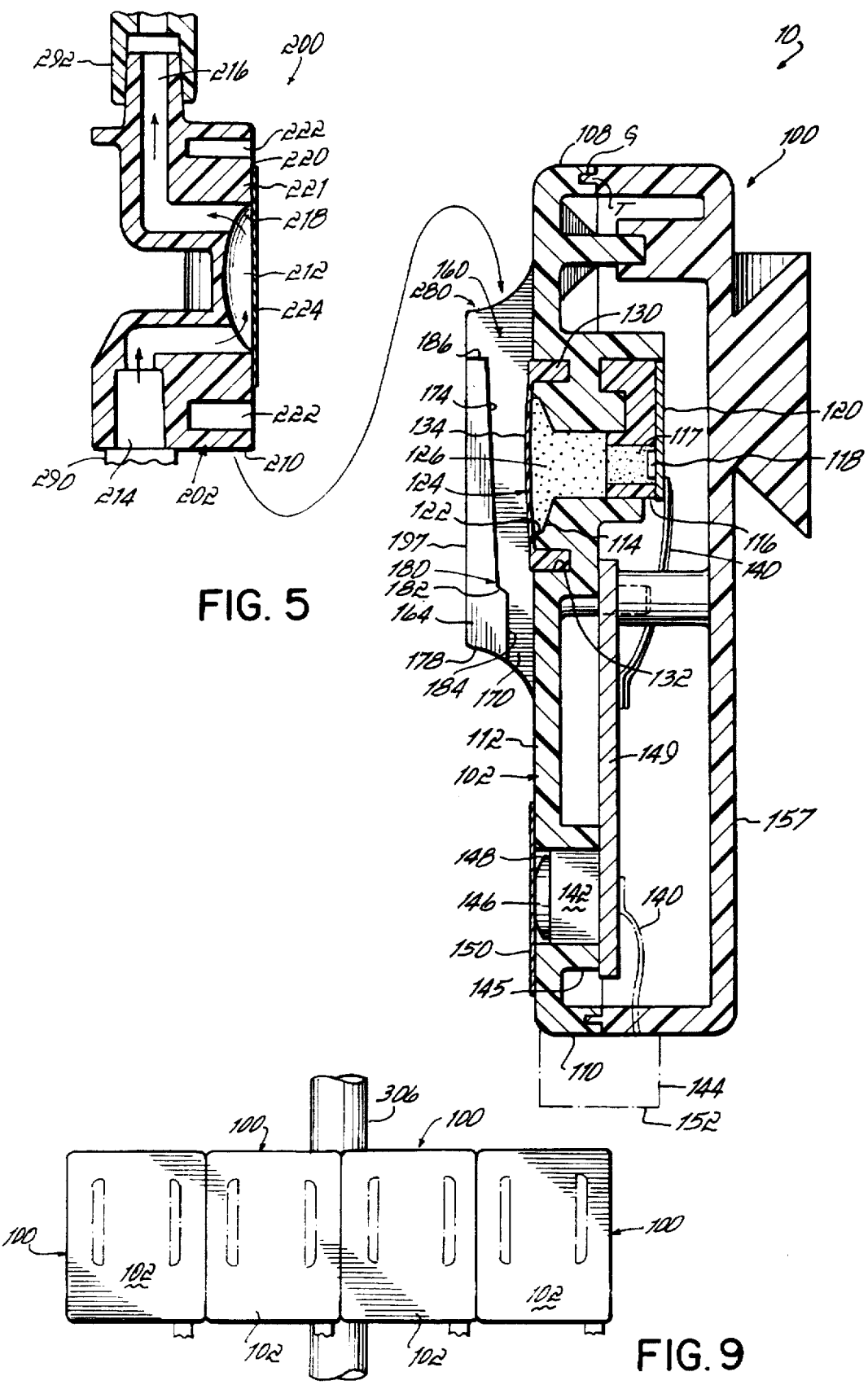
FIG. 5 is an exploded, cross-sectional view taken along lines 5—5 of FIG. 2.
FIG. 9 is a front diagrammatic view of a plurality of the transducers of FIG. 1 in pole-mounted position.
Figure 8:
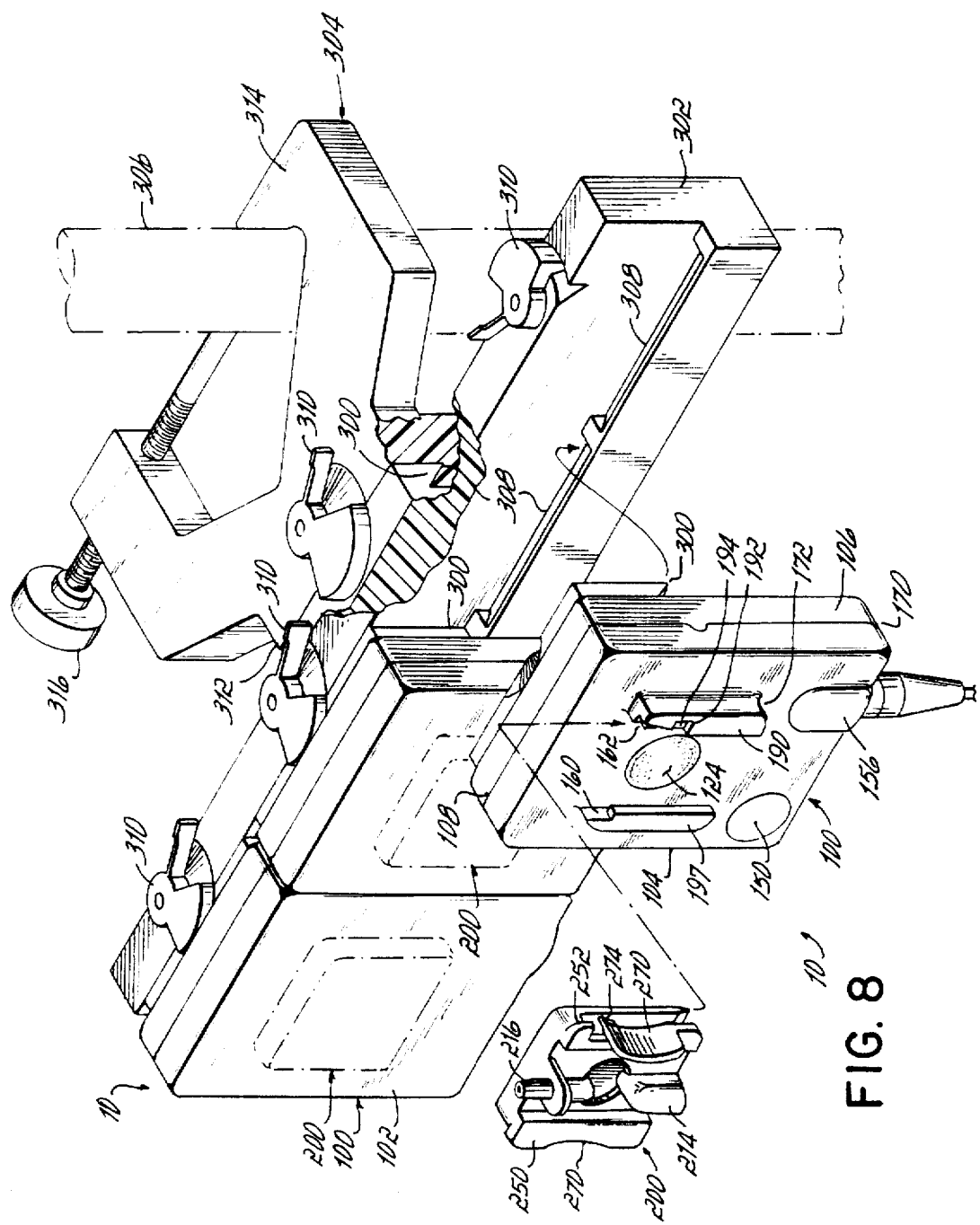
FIG. 8 is an exploded diagrammatic view of a pole mount arrangement for a plurality of the transducers of FIG. 1.

Extending from behind face 112 is an integral sensor chamber 114 (FIGS. 4 and 5). Permanently attached within sensor chamber 114, such as by adhesive (not shown), is a plastic chimney 116 filled with cured gel 117 at the bottom of which is an integrated circuit sensor chip 118 mounted to printed circuit (PC) board substrate 120 with a small vent hole (not shown) therethrough to vent chip 118. PC board 120 contains appropriate circuitry thereon (not shown) and is affixed with chimney 116 to thus permanently associate sensor 118 with reusable component 100. At the upper end of chamber 114 through face 112 is an aperture 122. Permanently mounted over aperture 122 is an elastomeric reusable diaphragm 124 such as of molded polyurethane.

Additional gel 126 is inserted in liquid state into chamber 114 between diaphragm 124 and chimney 116 via fill port 128 to bring diaphragm 124 into pressure communication, via gels 126 and 117, with sensor 118. Port 128 is sealed such as by insertion of a tightly-fitting ball or screw or the like (not shown) to thus slightly distend diaphragm 124 and gel 126 is cured.

The edge 130 of diaphragm 124 defines a cylindrical collar that is fitted into annular groove 132 in face 112 about aperture 122 to hold diaphragm 124 to support 102 with the front face or surface 134 of reusable diaphragm 124 exposed in, or bulging just slightly above, the plane of front face 112. A plurality of conductors 140 interconnect calibration test switch 142 and connector 144 to PC board substrate 120 circuitry and sensor 118, all behind face 112 of plate 102. Switch 142 is fitted within open-bottom well 145 formed into face 112 with switch button 146 being accessible at aperture 148 through plate face 112 in the lower left corner thereof as seen from the front (FIG. 3). Conductors 140 could be separate wires or ribbon cable and/or conductive traces (not shown) on a switch-supporting PC board 149. Placed over aperture 148 is a compliant, polycarbonate membrane 150 to protect switch 142 and to allow actuation thereof such as by gripping of reusable component 100 between the thumb and forefinger (not shown) in the area of membrane 150 and compressing same. Membrane 150 is adhesively held along its perimeter to the edge of well 145 defined at aperture 148. Actuation of switch 142 provides a calibration test as generally described in U.S. Pat. No. 4,760,730, the disclosure of which is incorporated herein by reference, but as a directly integral part of the reusable component, rather than as a separate component.

To electrically connect to a monitor (not shown), connector 144 is provided at the bottom right of component 100 as seen from the front (FIGS. 2 and 3). Connector 144 may have a cylindrical plastic shell 152 with female pin-receiving connectors 154 therein and housed in a bulbously protruded area 156 of component 100. Connector 144 is accessible through connector port 158 in bottom edge 110. Connector 144 may form part of a two-connector set as shown in U.S. Pat. No. 5,167,522. An opaque plastic back plate 157 may be secured, such as by adhesive (not shown), over the back side of plate 102 to enclose the above-mentioned components, with a tongue T and groove G arrangement (see FIG. 4) between their connecting sides to thus define a complete housing. Alternatively, plate 157 may be press-fit to plate 102 by interaction of the tongue T and groove G and pins P and bosses B shown in FIG. 4. Also, the housing defined by plate 102 and back 157 may be vented, such as via a small through-hole or path (not shown) formed therein. A filter member (also not shown) may be included with the through-hole or path. Additionally, plate 157 is adapted to be mountable to a pole and thus includes structure to connect to a pole-mount as will be discussed, thereby eliminating the extra part and manipulation required by the operator to mount the reusable sensor portion to the support plate.

To mount disposable dome component 200 to reusable sensor housing 100 as will be described, plate 102 is provided with channel members which, in the preferred embodiment shown in FIGS. 1–9, are defined by a pair of channels 160,162 disposed to opposite left and right sides of reusable diaphragm 124 as seen from the front (FIG. 3). Each channel 160,162 is defined behind a respective outer front wall 164,166 associated with plate 102. To this end, outer front walls 164,166 are generally parallel to, but spaced from, front face 112 and held thereto by interconnecting side walls 170,172, respectively, to thus define generally linear and parallel paths or channels 160,162 between front face 112 and the underside 174,176 of each respective outer front wall 164,166. The lateral extent of each channel 160,162 is further defined by side walls 170,172, respectively.

The underside 174 or 176 of outer front wall 164 or 166 may be slightly angled with a draft (such as for molding) as it progresses from near the top edge 108 of plate 102 towards the bottom edge 110 thereof (FIG. 5). The draft narrows somewhat the width of the channel 160 or 162 in the direction of insertion travel of the dome 200. For purposes described hereinafter, camming structure is provided at the terminal or bottom end 178 of the channels 160,162. The camming structure in the preferred embodiment shown is provided by camming ramp 180° comprised of a 45° ramp 182 and a trailing step 184 to define a generally precise channel width $W_c$ thereat (see FIG. 7A). The top edge 186 of each wall 164,166 is exposed. The bottom end 178 of each channel 160 or 162 may be closed off (not shown) but is advantageously left open as shown so that debris does not accumulate in the channels.

With particular reference to FIGS. 3 and 4, it may be seen that the outer surface 190 of right side channel outer front wall 166 includes a depression such as tab-receiving slot 192 formed therein (over side wall 172). Slot 192 extends into alleyway 194 also formed in outer surface 190 (over channel 162) which in turn ends adjacent chamfer 196 of outer front wall 166 all for purposes to be described hereinafter. Outer surface 190 is otherwise generally planar and parallel to front face 112. Outer surface 197 of left side, outer front wall 164 is similarly planar and parallel to front face 112. Although shown as a single member, support plate 102 could be made of more than one piece or element joined together to provide the structural and functional relationship of the elements described above.

With particular further reference to FIGS. 5 and 6, disposable dome 200 is of clear or translucent plastic and may be seen as having a central body portion 202 defined between left and right edges 204,206 and top and bottom edges 208,210 to define a generally rectangular shape to central body portion 202. Formed centrally through the back of body portion 202 is a fluid path well 212 which communicates through an inlet port 214 extending up out of the front of well 212 and accessible along bottom edge 210 and outlet pipe 216 extending up out of the front of well 212 and beyond top edge 208. Inlet and outlet 214 and 216 cooperate to extend fluid path 212 through disposable dome 200. Fluid path 212 is accessible through a large aperture 218 along the back side 220 of central portion 202. Well 212 and aperture 218 are defined by a cylindrical wall 221 in central portion 202 with cavities 222 defined between wall 221 and edges 204,206,208,210. Alternatively, cavities 222 could be filled with plastic. Either way, back side 220 of dome 200 functions to define a flat or plate-like surface to dome 200 to match up to planar face 112 of plate 102.

Extending across aperture 218 along bottom side 220 is an elastomeric diaphragm 224 permanently affixed to central portion 202 and providing a pressure transmitting, fluid impervious wall to seal the fluid path within dome 200. Diaphragm 224 could be a molded polyurethane, like diaphragm 124 with a collar (not shown) mounted within an annular recess or groove (also not shown) about aperture 218. Alternatively, diaphragm 224 could be a sheet of urethane film material, the peripheral edge of which is either adhesively or thermally bonded to the edge of aperture 218, or is held into a groove (not shown) about aperture 218 such as by a compression ring (also not shown).

To mount dome 200 to reusable component 100, the dome is provided with a pair of edges that mate with the channel members of the reusable component. To this end, extending outwardly from opposite left and right sides (as viewed in FIGS. 2 and 4) of central portion 202 (from edges 204 and 206, respectively) and to either side of diaphragm 224 are generally linear and parallel left and right mounting wings 230,232 situated to be matingly received within channels 160,162 of reusable plate 102 such as to place disposable diaphragm 224 into confronting relationship with reusable diaphragm 124. Bottom end 234 of each wing 230,232 is chamfered as at 235 (see FIG. 7A) for purposes to be described hereinafter. Bottom end 234 just above chamfer 235 has a generally precise thickness or width, which in combination with diaphragms 224 and 124, is closely equal to channel width $W_c$, so as to hold the diaphragms in proper pressure communicating relationship. Further camming structure is defined at top or distal end 236 of each wing. In the preferred embodiment shown, the further camming structure is provided by camming ramp 240 which, like the camming ramp 180 within channels 160 and 162, is comprised of a 45° ramp 242 and a trailing step 244 to define a precise width $W_w$ of wing 230 or 232 in the area of trailing step 244. In this regard, the thickness or width of the channels 160,162 at their openings near the top edge 108 of plate 102 cooperate with diaphragms 224 and 124 to closely equal width $W_w$ so as to, in addition or alternatively to the holding ability of bottom end 234 and width $W_c$, hold the diaphragms in proper pressure communicating relationship.

Camming ramp 180 and camming ramp 240 are situated on respective ones of the reusable component 100 and disposable dome 200 so as to engage their respective counterpart structures near the tailing end of the travel of dome 200 as the wings 230,232 are slidably received into the channels 160,162 of the reusable component 100. In this manner, as the dome 200 travels generally linearly in a direction generally parallel to the reusable diaphragm 124 into reusable component 100, there may be a slight space (or just loose, sliding contact) between the diaphragms 124 and 224 so as not to harmfully abrade at least diaphragm 124. As dome 200 nears the end of its longitudinal travel into reusable component 100, wings 230,232 are driven, in a somewhat axial direction, towards face 112 and diaphragm 124 of plate 102 such that disposable diaphragm 224 is driven into abutting relationship with reusable diaphragm 124 to provide a proper pressure communicating relationship therebetween. To limit the extent of travel of dome 200 relative to plate 102, a closing wall 246 may be provided at distal or top end 236 of each wing 230,232 which closing wall 246 will abut into top edge 186 of outer front walls 164 or 166.

To facilitate use of dome 200 with reusable plate 102, a second set of wings 250,252 may be provided. Wings 250,252 also extend from edges 204 and 206 but spaced above respective ones of mounting wings 230,232 to define wall-receiving spaces 254,256 (FIGS. 4 and 7). As is thus apparent, wing pairs 230,250 and 232,252 cause spaces 254,256 to function as attachment structure channels of the dome to receive respective ones of outer walls 164 and 166 which function as wing-like attachment structure of the reusable component as dome 200 is slidingly received into reusable component 100. Second wings 250,252 extend generally outwardly so as to substantially overlie outer walls 164 and 166 to provide the aesthetic appearance of a single unit when components 200 and 100 are mounted together as shown in FIG. 1. Additionally, wings 250,252 may also provide a barrier to debris from entering channels 160,162 when dome 200 is mounted to plate 102.

As seen in FIGS. 2 and 6, lateral edges 260,262 of second wings 250,252, respectively, may be indented as at 264 and 265, respectively, to provide finger and thumb gripping areas for the user (not shown) to grip dome 200 to mount and dismount same from reusable component 100. Finger-gripping portions 264, 265 may be textured (such as by grooving, serrating or knurling) to facilitate such manipulation by the user. With particular reference to FIG. 2, it may be seen that indented finger-gripping portion 265 of right side second wing 252 may actually be provided by resilient locking or flexing paddle 270 having an indented shape and a textured surface to simulate indented portion 264 of left side second wing 250. Supported at a terminal end 272 of paddle 270 is a locking tab 274 such that tab 274 defines a projection resiliently attached to dome 200 and spaced above and depending towards wing 232. Locking paddle 270 extends from a hinging area 276 nearer to the bottom end 278 of wing 252 such that by flexing action of locking paddle 270, locking tab 274 is movable towards central portion 202 near to the top end 280 of wing 252.

As dome 200 is slidably received into reusable component 100, locking tab 274 may bear against chamfer 196 (FIG. 3) of outer wall 166 to thereby flex paddle 270 leftwardly. As dome 200 moves further in its travel, tab 274 passes onto alleyway 194 and then, at the end of the travel of dome 200, snaps rightwardly back out into slot 192 (with a clicking sound) to lock dome 200 into position on plate 102 with diaphragms 224 and 124 in confronting, pressure transmitting relationship (FIG. 7C). To remove dome 200, the user (not shown) may grip dome 200 with the thumb (not shown) in indented portion 264 and the forefinger (not shown) against locking paddle 270 compressing same so that locking tab 274 comes away from tab-receiving slot 192, and then sliding upwardly towards the top edge 108 of plate 102 to withdraw dome 200 therefrom.

Dome 200 may be provided with a fast-flush device 290 coupled to inlet port 214 (such as the fast flush device shown in U.S. Pat. No. 5,171,230) and a stopcock 292 coupled to outlet pipe 216. Flush device 290 may then be connected by tubing 294 to a source of saline (not shown) and stopcock 292 may be connected by further tubing 296 to a catheter 298 (FIG. 2) to be placed within the patient's circulatory system (not shown) to thus monitor the pressure thereof as in the case of sensor 102 in FIG. 7 of U.S. Pat. No. 5,221,271, the disclosure of which is incorporated herein by reference. While the use of two wings and two channels is shown in the preferred embodiment, at least only one of each may be employed. Also, the outer front walls may be coplanar with front face 112 with appropriate adjustment in the elevation of either diaphragm 124 or mounting wings 230,232, by way of example. Further, while slot 192 is shown on support 102 and locking tab 274 on dome 200, they could be reversed.

With reference to FIGS. 7A-7C (in which channel 160 and its associated walls are removed for sake of clarity), there is shown diagrammatically the mounting of dome 200 to reusable component 100 in accordance with the various aspects of the present invention. In FIG. 7A, dome 200 is just about to be mounted to plate 102 with wing 232 just beginning to enter channel 162 in a direction along the downwardly-directed arrow A. Thus, dome wing 232 is coming into channel 162 from the direction of top edge 108 of plate 102. Top end 186 of outer front wall 166 may be impacted by chamfered wall 235 at the proximal end of wing 232 to help force wing 232 into the space or channel 162 defined behind outer front wall 166. In FIG. 7A, second wing 252 is spaced above and away from top surface 190 of front wall 166.

As dome 200 is continued in its downward progression towards bottom wall 110, as in FIG. 7B, most of the length of wing 232 passes into channel 162 and wing 252 passes over front 190 of front wall 166. In this progression of travel, it may be seen that there may be a slight space or at least a loose or sliding contact (indicated by the letter S) between diaphragms 224 and 124 so as to avoid damaging or chafing the diaphragms, and especially diaphragm 124 which is intended to be reusable with several of domes 200. Near the end of the travel, chamfer 235 hits against ramp 182 of camming ramp 180 to start to drive the proximal end of wing 232 towards face 112 and diaphragm 124. At about the same time, camming ramp 242 impacts against top edge 186 to also drive the distal end of wing 232 towards face 112 and diaphragm 124 in which event the spacing S between diaphragms 224 and 124 begins to decrease (or the loose contact begins to tighten up). Also, tab 274 impinges wall chamfer 196 (FIG. 3) and flexes paddle 270 inwardly so as to allow tab 274 to travel into alleyway 194.

In the end of the travel of dome 200 into reusable component 100 in FIG. 7C, the proximal end of wing 232 is situated below and against trailing end 184 and the top end 186 of outer wall 166 is situated above and against trailing end 244 of wing camming ramp 240 such that wing 232 has been driven towards plate face 112 and diaphragms 224 and 124 have been driven into abutting relationship to provide the desired pressure communicating relationship therebetween. Also, in this terminal end of the travel, second wing 252 is positioned so as to substantially completely overlie top surface 190 of front wall 166, and paddle 270 has gone back towards its original position with tab 274 locked into slot 192. The same arrangement of travel as shown in FIGS. 7A–7C occurs simultaneously between wing 230 and channel 160.

In use, dome 200 is slidably mounted to reusable component 100 as above described and appropriate tubing 294,296 and catheter 298 are employed to couple fluid path 212 of transducer 10 to a patient and connector 144 utilized to couple signals representing the patient's blood pressure, for example, with a monitor in an otherwise conventional manner such as FIG. 7 of the aforementioned U.S. Pat. No. 5,221,271. After the use for that patient is completed, or should dome 200 need to be replaced for any reason, dome 200 may be simply removed by depressing locking paddle 270 and sliding dome 200 out of channels 160,162 of reusable component 100 and the dome 200 disposed of (with or without tubing). Either new tubing may be provided, or the old tubing used, with a new dome 200 as appropriate, depending upon the patient's situation, and new dome 200 slidably remounted to reusable component 100 as previously described. In many situations, it may be desirable to monitor more than one pressure. In this event, multiple transducers 10 may be utilized as will now be described with reference to FIG. 8.

Back plate 157 of each reusable component may be provided with a mounting structure 300 to mount component 100 to an intravenous pole or other support. To this end, structure 300 is mounted to a support frame 302 which, in turn, is mounted to a pole-mount clamp 304 secured to a pole 306. The mounting frame 302 includes a plurality of receptacles 308 to receive the respective support structure 300 of a plurality of reusable components 100 which are then locked in place by actuation of the locking handle 310 on frame 302. Frame 302 also includes an identical mounting structure 300 receivable in an identical receptacle 308 and held thereto by actuation of handle 310 on the proximal end 312 of pole mount clamp 304. Clamp 304 is held to pole 306 in conventional manner such as by interaction of yoke 314 and screw 316 about pole 306. Alternatively, one reusable component 100 may be mounted directly to the pole mount clamp 304 and frame 302 dispensed with. Further alternatively, or additionally, each plate 102 could be provided as modular interconnecting plates as shown in aforementioned U.S. Pat. No. 5,417,395.

Due to the rectangular nature of plate 102, it may be seen that when a plurality of reusable components are mounted as above-described (see FIG. 9), they give the appearance of being a solid set of units, more or less, and may thus be considered as being modular in that any one of the reusable components 100 may be placed in any one of the positions defined by receptacles 308 available on frame 302. Domes 200 may be mounted to their respective reusable components 100 either before or after the related component 100 is connected to frame 302. In any event, it may be seen that transducer 10 includes as part of the reusable component, structure by which to be mountable to a pole without the need for an additional support plate as was typical of the prior art.

With reference to FIGS. 10–14, and in accordance with the principles of the present invention, alternative constructions of two-component disposable dome and combined reusable sensor/support plate transducers are shown. To this end, a first alternative embodiment is shown in FIGS. 10 and 11 in which transducer 400 includes rigid mounting plate 401 having a generally planer front face 402. Extending along the length of right side edge 404 of plate 400 is a rib 406 receivable in slot 408 along the left side edge 410 of another identical transducer 400 or mounting plate 401 and locked thereto by action of pivoting arms 412 pivotally mounted to plate 401 all as described in previously mentioned application Ser. No. 08/407,903 and U.S. Pat. No. 5,417,395, the disclosures of both of which have been incorporated herein by reference. Also, extending from the back side of plate 401 is shelf 413 by which plate 401 is mountable to the intravenous pole 306 (see FIG. 8) or other external structure by way of well known clamping mechanisms (such as pole-clamping mechanism 85 in the aforesaid application and patent). Alternatively, shelf 413 could be replaced with mounting structure 300 to be pole-mountable as described above.

Rigid plate 401 has an aperture 414 formed therethrough with reusable diaphragm 416 affixed to plate face 402 across aperture 414. A transducer sensor 418 (FIG. 11) is secured to plate 401 behind aperture 414 and placed into pressure communication with diaphragm 416, such as via a gel-filled recess, to fully perform the function of a reusable transducer component. Wires 420 extend from sensor 418 to be coupled to a monitor (not shown). Sensor 418 may alternatively have electrical connectors extending therefrom for releasable attachment to a cable coupled to the monitor. The construction of sensor 418 and diaphragm 416 and the reusable transducer portions may be as described above in connection with FIGS. 1–9 and/or as disclosed in U.S. Pat. No. 4,920,972, the disclosure of which is incorporated herein by reference, and previously mentioned U.S. Pat. No. 5,417,395.

To use sensor 418, reusable diaphragm 416 is to be placed into confronting engagement with the diaphragm 422 of a disposable fluid dome 424 (diaphragm 422 is secured to dome 424 but is shown separated therefrom in FIG. 10 for explanatory purposes). Fluid dome 424 includes an inlet 26 and an outlet 28 in fluid communication with a path extending through dome 424 and sealed off by diaphragm 422 as in the case of dome 200 above-described.

To releasably hold dome 424 to reusable mounting plate 401, attachment structure is provided on both plate 401 and dome 424. The attachment structure of plate 401 is provided by channel members defined as a pair of slots 430 parallel to right and left side edges 404 and 410 of rigid plate 401 and extending through face 402 on opposite sides of aperture 414 and diaphragm 416. Slots 430 are sized and positioned to receive locking arms 434 pivotally connected by pivot members 436 to fluid dome 424. Arms 434 have inwardly facing hooks 438 thereon. As locking arms 434 are inserted in and through slots 430, hooks 438 ride over inner edges 440 of slots 430, and when disposable dome diaphragm 422 is in confronting, pressure communicating engagement with the reusable portion diaphragm 416, hooks 438 emerge through rigid plate 401 and locking arms 434 resume their undeformed shape thereby securely locking disposable dome 424 to mounting plate 401.

To remove disposable dome 424, proximal ends 442 of locking arms 434 are inwardly depressed to pivot the distal ends 438 outwardly, thereby disengaging hooks 438 from the slot inner edges 440 whereby dome 424 may be pulled free of the mounting plate 400.

In a second alternative embodiment shown in FIG. 12, locking arms 434 could be extended as at 434' to substantially lengthen slots 430. For this purpose, pivot members 436 are replaced with connecting plate 436', although use of dome 424 in FIG. 12 is the same as in FIGS. 10 and 11. Still further alternatively, a "ski-boot" foot and latching arm structure may be used as shown in FIG. 13. To this end, plate 401 and reusable portion diaphragm 416 continue to remain unchanged from that described above. However, the locking structure of disposable fluid dome 424 is replaced with an outwardly facing L-shaped foot 450 connected to one side of connecting plate 436' and extending forwardly therefrom, and an extended length latch member arm 434" on the other side of the connecting plate 436', which is the same as that described above for arm 434' but with a lever arm 452 attached thereto for a purpose to be described.

To secure fluid dome 424 to mounting plate 401 in the embodiment of FIG. 13, dome 424 is pivoted onto its side so that the free end 454 of foot 450 may be inserted into one of slots 430. Fluid dome 424 is then pivoted towards plate face 402 until latching member 434" locks into the other slot 430 thereby placing the respective diaphragms in confronting pressure communicating engagement. To remove the disposable fluid dome 424 of FIG. 13, lever arm 452 is lifted to disengage latching arm 434" from mounting plate 401 and fluid dome 424 is pivoted, whereby foot 450 may be removed from slot 430 and fluid dome 424 lifted from mounting plate 401. Although the locking structure of fluid dome 424 in FIGS. 12 and 13 is shown with connecting plate 436' extending from the front of fluid dome 424, it will be readily appreciated that the connecting plate 436' could be formed along the side or from the rear of the fluid dome.

With reference to FIG. 14, another embodiment of the transducer 400 of FIG. 10 is shown utilizing the simplified wing/channel arrangement of the transducer 10 of FIG. 1. To this end, the channel members are defined in plate 401 by L-shaped walls 460 extending along slots 430 and an outer front wall 462 attached to each wall 460 to define a receptacle or channel 464 therebehind and communicating to each slot 430. The fluid dome 424 is modified such that the edges define wings 470 extending outwardly of dome 424 and in the same plane to be slidingly received into the receptacles 464 to thus hold the respective diaphragms into confronting engagement. Wings 470 may be part of a plate 472 formed along the bottom or back side of dome 424. Use of transducer 400 of FIG. 14 is like that of transducer 10 of FIG. 1.

By virtue of the foregoing, there is thus provided a medical pressure transducer in which the reusable portion and support plate are combined to eliminate a part and its extra manipulation. Further, such a transducer is provided in which the dome and reusable component easily and simply mate together, such as by relative sliding action in a preferred embodiment. Features are provided to enhance the pressure transmitting relationship between the diaphragms and to facilitate operator use of the transducer. The invention in its broader aspects is not, however, limited to the specific details, representative apparatus and methods and illustrative examples shown and described.

What is claimed is:

1. A medical pressure transducer comprising:
    a disposable dome having a fluid path adapted to be coupled to a patient, a dome diaphragm coupled to the fluid path, and at least one edge disposed to one side of the dome diaphragm; and
    a reusable component having a support, a pressure sensor permanently associated with the support, a reusable diaphragm in pressure communication with the sensor, and at least one channel member disposed to one side of the reusable diaphragm and slidably receiving the dome edge along a generally linear path which is generally parallel with the reusable diaphragm such that the dome diaphragm is brought into confronting relationship with the reusable diaphragm on mating reception of the edge into the channel member by sliding the dome edge in a direction which is generally linear and generally parallel to the reusable diaphragm.

2. The transducer of claim 1, the at least one channel member defining a channel and the dome edge defining a mounting wing extending to the one side of the dome diaphragm, the wing and channel being configured to be slidably received together so as to slide the dome diaphragm into confronting relationship with the reusable diaphragm.

3. The transducer of claim 2 further comprising camming structure associated with at least one of the channel and the dome wing by which to drive the dome diaphragm into the reusable diaphragm as the dome wing is slidingly received into the channel.

4. The transducer of claim 3 wherein the camming structure is associated with the channel.

5. The transducer of claim 4 further comprising second camming structure associated with the wing.

6. The transducer of claim 4 wherein the camming structure is defined at a bottom end of the channel.

7. The transducer of claim 3 wherein the camming structure is associated with the wing.

8. The transducer of claim 7 wherein the camming structure is defined at a top end of the wing.

9. The transducer of claim 3 wherein the camming structure includes a step.

10. The transducer of claim 9 wherein the camming structure includes a ramp.

11. The transducer of claim 3 wherein the camming structure includes a ramp.

12. The transducer of claim 3 further comprising a depression and a projection each associated with a respective one of the support and the dome, the depression and the projection being relatively positioned such that the depression receives the projection as the wing is slidably received into the channel to lock the dome diaphragm into confronting relationship with the reusable diaphragm.

13. The transducer of claim 12 further comprising at least one outer front wall with the channel defined therebehind, and a second wing spaced above the mounting wing to define a wall-receiving space for the outer front wall.

14. The transducer of claim 2 further comprising a tab resiliently attached to the dome.

15. The transducer of claim 2 further comprising a depression and a projection each associated with a respective one of the support and the dome, the depression and the projection being relatively positioned such that the depression receives the projection as the wing is slidably received into the channel to lock the dome diaphragm into confronting relationship with the reusable diaphragm.

16. The transducer of claim 15 the depression being a tab-receiving slot associated with the support and the projection being a locking tab associated with the dome.

17. The transducer of claim 16 further comprising at least one outer front wall with the channel defined therebehind, the tab-receiving slot being defined in the outer front wall.

18. The transducer of claim 16 further comprising a locking paddle associated with the dome, the locking tab being supported by the locking paddle.

19. The transducer of claim 15 further comprising at least one outer front wall of the reusable component with the channel defined therebehind, and a second wing on the dome spaced above the mounting wing to define a wall-receiving space for the outer front wall.

20. The transducer of claim 2 further comprising at least one outer front wall of the reusable component with the channel defined therebehind, and a second wing on the dome spaced above the mounting wing to define a wall-receiving space for the outer front wall.

21. The transducer of claim 20 further comprising a tab associated with the second wing and receivable in a tab-receiving slot defined in the reusable component.

22. The transducer of claim 21, the tab-receiving slot being defined in the outer front wall.

23. The transducer of claim 21 further comprising a flexing paddle associated with the dome, the tab being supported by the flexing paddle.

24. The transducer of claim 20 further comprising a finger gripping portion defined in the second wing.

25. The transducer of claim 24 further comprising a flexing paddle associated with the dome.

26. The transducer of claim 25 further comprising a tab associated with the flexing paddle and received in a tab-receiving slot defined in the reusable component.

27. The transducer of claim 25, the finger gripping portion being defined by the flexing paddle.

28. The transducer of claim 20 wherein the second wing extends parallel to the mounting wing.

29. The transducer of claim 2 wherein the reusable component includes two such channels and the disposable dome includes two such mounting wings.

30. The transducer of claim 29 wherein the channels are disposed to opposite sides of the reusable diaphragm and the wings are disposed to opposite sides of the dome diaphragm.

31. The transducer of claim 2 further comprising a calibration test switch associated with the support and electrically connected to the sensor.

32. The transducer of claim 2 wherein the support includes peripheral side edges that define a generally rectangular shape and a front face whereat the reusable diaphragm is exposed.

33. The transducer of claim 1 further comprising a calibration test switch associated with the support and electrically connected to the sensor.

34. The transducer of claim 1 wherein the support includes peripheral side edges that define a generally rectangular shape and a front face whereat the reusable diaphragm is exposed.

35. The transducer of claim 1 further comprising integral support structure for mating the reusable component to an external support.

36. A medical pressure transducer comprising a reusable component for use with a disposable dome having a fluid path adapted to be coupled to a patient, a dome diaphragm coupled to said fluid path, and at least one edge disposed to one side of said dome diaphragm, the reusable component comprising:

a support;

a pressure sensor permanently associated with the support;

a reusable diaphragm in pressure communication with the sensor; and at least one channel member disposed to one side of the reusable diaphragm and being configured to slidably receive said dome edge along a generally linear path which is generally parallel to the reusable diaphragm such that said dome diaphragm is brought into confronting relationship with the reusable diaphragm on mating reception of said edge into the channel member by sliding said dome edge in a direction which is generally linear and generally parallel to the reusable diaphragm.

37. The transducer of claim 36 wherein said dome edge defines a mounting wing extending to said one side of said dome diaphragm, the at least one channel member defining a channel configured to slidably receive said dome wing so as to slide said dome diaphragm into confronting relationship with the reusable diaphragm.

38. The transducer of claim 37 further comprising camming structure associated with the channel by which to drive said dome diaphragm into the reusable diaphragm as said dome wing is slidingly received into the channel.

39. The transducer of claim 38 wherein the camming structure is defined at a bottom end of the channel.

40. The transducer of claim 38 wherein the camming structure includes a step.

41. The transducer of claim 40 wherein the camming structure includes a ramp.

42. The transducer of claim 38 wherein the camming structure includes a ramp.

43. The transducer of claim 38 further comprising one of a depression and a projection associated with the support and positioned to receive a projection or be received in a depression, respectively, of said dome as said dome wing is slidably received into the channel to lock said dome diaphragm into confronting relationship with the reusable diaphragm.

44. The transducer of claim 37 further comprising one of a depression and a projection associated with the support and positioned to receive a projection or be received in a depression, respectively, of said dome as said dome wing is slidably received into the channel to lock said dome diaphragm into confronting relationship with the reusable diaphragm.

45. The transducer of claim 37 further comprising a tab-receiving slot associated with the support and positioned to receive a locking tab of said dome as said dome wing is slidably received into the channel to lock said dome diaphragm into confronting relationship with the reusable diaphragm.

46. The transducer of claim 45 further comprising at least one outer front wall with the channel defined therebehind, the tab-receiving slot being defined in the outer front wall.

47. The transducer of claim 37 wherein the reusable component includes two such channels disposed to opposite sides of the reusable diaphragm.

48. The transducer of claim 37 further comprising a calibration test switch associated with the support and electrically connected to the sensor.

49. The transducer of claim 37 wherein the support includes peripheral side edges that define a generally rectangular shape and a front face whereat the reusable diaphragm is exposed.

50. The transducer of claim 36 further comprising a calibration test switch associated with the support and electrically connected to the sensor.

51. The transducer of claim 36 wherein the support includes peripheral side edges that define a generally rectangular shape and a front face whereat the reusable diaphragm is exposed.

52. The transducer of claim 36 further comprising integral support structure for mating the reusable component to an external support.

53. A medical pressure transducer comprising a disposable dome for use with a reusable component having a support, a pressure sensor permanently associated with said support, a reusable diaphragm in pressure communication with said sensor and at least one channel member disposed to one side of said reusable diaphragm, the disposable dome comprising:

a body having an aperture defining a plane;

a fluid path adapted to be coupled to a patient, the fluid path extending into the body and communicating with the aperture;

a dome diaphragm coupled to the fluid path and extending across and sealing the aperture; and at least one generally linear edge disposed to one side of the dome diaphragm and extending generally in the plane defined by the aperture, the one edge configured to be slidably received into said reusable component channel member along a generally linear path which is generally parallel with said reusable diaphragm such that the dome diaphragm is brought into confronting relationship with said reusable diaphragm on mating reception of the one edge into said channel member by sliding the one edge in a direction which is generally linear and generally parallel to said reusable diaphragm.

54. The transducer of claim 53 wherein said channel member defines a channel, the dome edge defining a mounting wing extending to the one side of the dome diaphragm to be slidably received into said at least one channel so as to slide the dome diaphragm into confronting relationship with said reusable diaphragm.

55. The transducer of claim 54 further comrpising a tab resiliently attached to the dome.

56. The transducer of claim 54 further comprising one of a depression and a projection associated with the dome and positioned to receive a projection or be received in a depression of said reusable component as the dome wing is slidably received into said channel to lock the dome diaphragm into confronting relationship with said reusable diaphragm.

57. The transducer of claim 54 wherein the disposable dome includes two such mounting wings disposed to opposite sides of the dome diaphragm.

58. A medical pressure transducer comprising a disposable dome for use with a reusable component having a support, a pressure sensor permanently associated with said support, a reusable diaphragm in pressure communication with said sensor and at least one channel member defining a channel disposed to one side of said reusable diaphragm, the disposable dome comprising:

a fluid path adapted to be coupled to a patient;

a dome diaphragm coupled to the fluid path;

at least one generally linear edge disposed to one side of the dome diaphragm, the one edge defining a mounting wing extending to one side of the dome diaphragm and configured to be slidably received into said reusable component channel along a generally linear path which is generally parallel with said reusable diaphragm such that the dome diaphragm is brought into confronting relationship with said reusable diaphragm on mating reception of the mounting wing into said channel member by sliding the mounting wing in a direction which is generally linear and generally parallel to said reusable diaphragm; and camming structure associated with the dome wing by which to drive the dome diaphragm into said reusable diaphragm as the dome wing is slidably received into said channel.

59. The transducer of claim 58 wherein the camming structure is defined at a top end of the wing.

60. The transducer of claim 58 wherein the camming structure includes a step.

61. The transducer of claim 60 wherein the camming structure includes a ramp.

62. The transducer of claim 58 wherein the camming structure includes a ramp.

63. The transducer of claim 58 further comprising one of a depression and a projection associated with the dome and positioned to receive a projection or be received in a depression of said reusable component as the dome wing is slidably received into said channel to lock the dome diaphragm into confronting relationship with said reusable diaphragm.

64. The transducer of claim 63 wherein said channel is defined behind an outer front wall of said reusable component, the transducer further comprising a second wing spaced above the mounting wing to define a wall-receiving space for said outer front wall.

65. A medical pressure transducer comprising a disposable dome for use with a reusable component having a support, a pressure sensor permanently associated with said support, a reusable diaphragm in pressure communication with said sensor and at least one channel member defining a channel disposed to one side of said reusable diaphragm, the disposable dome comprising:

a fluid path adapted to be coupled to a patient;

a dome diaphragm coupled to the fluid path;

at least one generally linear edge disposed to one side of the dome diaphragm, the one edge defining a mounting wing extending to one side of the dome diaphragm and configured to be slidably received into said reusable component channel along a generally linear path which is generally parallel with said reusable diaphragm such that the dome diaphragm is brought into confronting relationship with said reusable diaphragm on mating reception of the mounting wing into said channel member by sliding the mounting wing in a direction which is generally linear and generally parallel to said reusable diaphragm; and a locking tab associated with the dome and positioned to be received in a tab-receiving slot of said reusable component as the dome wing is slidably received into said channel to lock the dome diaphragm into confronting relationship with said reusable diaphragm.

66. The transducer of claim 65 wherein said channel is defined behind an outer front wall of said reusable component, the transducer further comprising a second wing spaced above the mounting wing to define a wall-receiving space for said outer front wall.

67. The transducer of claim 65 further comprising a locking paddle associated with the dome, the locking tab being supported by the locking paddle.

68. The transducer of claim 67 wherein the locking tab is supported at a terminal end of the locking paddle.

69. A medical pressure transducer comprising a disposable dome for use with a reusable component having a support, a pressure sensor permanently associated with said support, a reusable diaphragm in pressure communication with said sensor and at least one channel member defining a channel disposed to one side of said reusable diaphragm, wherein said channel is defined behind an outer front wall of said reusable component, the disposable dome comprising:

a fluid path adapted to be coupled to a patient;

a dome diaphragm coupled to the fluid path;

at least one generally linear edge disposed to one side of the dome diaphragm, the one edge defining a mounting wing extending to one side of the dome diaphragm and configured to be slidably received into said reusable component channel along a generally linear path which is generally parallel with said reusable component channel along a generally linear path which confronting relationship with said reusable diaphragm on mating reception of the mounting wing into said channel member by sliding the mounting wing in a direction which is generally linear and generally parallel to said reusable diaphragm; and a second wing spaced above the mounting wing to define a wall-receiving space for said outer front wall.

70. The transducer of claim 69 further comprising a tab associated with the second wing and receivable in a tab-receiving slot defined in the reusable component.

71. The transducer of claim 70 further comprising a flexing paddle associated with the dome, the tab being supported by the flexing paddle.

72. The transducer of claim 71 wherein the tab is supported at a terminal end of the flexing paddle.

73. The transducer of claim 69 further comprising a finger gripping portion defined in the second wing.

74. The transducer of claim 73 further comprising a flexing paddle associated with the dome.

75. The transducer of claim 74 further comprising a tab associated with the flexing paddle and receivable in a tab-receiving slot of said reusable component.

76. The transducer of claim 75 wherein the tab is supported at a terminal end of the flexing paddle.

77. The transducer of claim 75, the finger gripping portion being defined by the flexing paddle.

78. The transducer of claim 69 wherein the second wing extends parallel to the mounting wing.

79. A reusable medical pressure transducer component for use with a disposable medical pressure transducer dome having a disposable diaphragm for pressure communication and a pair of edges disposed to different sides of the dome, the reusable medical pressure transducer component comprising:

a support;

a sensor permanently associated with the support;

a reusable diaphragm is pressure communication with the sensor; and a pair of channel members associated with the support and being configured to slidably receive respective ones of said pair of edges of the dome along a generally linear path which is generally parallel to the reusable diaphragm, the reusable diaphragm being disposed between the pair of channel members such that the channel members bring said disposable diaphragm into confronting pressure transmitting relationship with the reusable diaphragm on mating reception of said respective ones of said pair of edges into the channel members by sliding said pair of edges in a direction which is generally linear and generally parallel to the reusable diaphragm.

80. The component of claim 79 further comprising outer front walls, the channel members being defined therebehind.

81. The component of claim 79 in combination with the disposable dome and wherein the channel members define confronting channels, the edges of the disposable dome being defined by a pair of wings extending from opposing sides of the dome for sliding engagement with the confronting channels for slidably placing the disposable diaphragm in pressure communication with the reusable diaphragm.

82. The component of claim 79 further comprising support structure for mounting the component to an external support.

83. A disposable medical pressure transducer dome for use with a reusable component having a support, a pressure sensor permanently associated with said support, a reusable diaphragm in pressure communication with said sensor, and a pair of channels disposed to opposite sides of said reusable diaphragm, said dome comprising:

a body having an aperture defining a plane;

a fluid path adapted to be coupled to a patient, the fluid path extending into the body and communication with the aperture;

a dome diaphragm coupled to the fluid path and extending across and sealing the aperture; and a pair of generally linear wings extending outwardly to opposite sides of the dome diaphragm and generally in the plane defined by the aperture, the wings being configured to be slidably received in respective ones of said reusable component channels along a generally linear path which is generally parallel with said reusable diaphragm such that the dome diaphragm is slidably received into confronting relationship with said reusable diaphragm by sliding the wings in a direction which is generally linear and generally parallel to said reusable diaphragm.

84. The dome of claim 83, the wings extending generally in a plane.

85. The dome of claim 83 further comprising a plate supporting the dome diaphragm, the plate defining the pair of wings.

86. A medical pressure transducer comprising a disposable dome for use with a reusable component having a support, a pressure sensor permanently associated with the support, a reusable diaphragm in pressure communication with the sensor and attachment structure, the disposable dome comprising:

a body having an aperture defining a plane;

a fluid path adapted to be coupled to a patient, the fluid path extending into the body and communication with the aperture;

a dome diaphragm coupled to the fluid path and extending across and sealing the aperture; and dome attachment structure including at least first and second parallel wings associate with the dome, the at least first wing extending generally in the plane defined by the aperture, the dome attachment structure being configured to be slidably received into said reusable component attachment structure along a generally linear path which is generally parallel with said reusable diaphragm such that the dome diaphragm is slidably received into confronting relationship with said reusable diaphragm upon mounting the dome to said reusable component by sliding the at least first wing in a direction which is generally linear and generally parallel to said reusable diaphragm.

87. A medical pressure transducer comprising a reusable component for use with a disposable dome having a fluid path adapted to be coupled to a patient and a dome diaphragm coupled to said fluid path, the reusable component comprising:

a support adapted to mate with said dome;

a pressure sensor permanently associated with the support;

a reusable diaphragm in pressure communication with the sensor, the support adapted to receive said dome so as to bring said dome diaphragm into confronting relationship with the reusable diaphragm when said dome is slid into the support in a generally linear direction which is generally parallel to the reusable diaphragm; and a mount adapted to attach the support to a pole-clamp.

88. The transducer of claim 87, the means for attaching being a shelf extending generally perpendicular relative to a face of the support.

89. A medical pressure transducer comprising:

disposable dome having a fluid path adapted to be coupled to a patient, a dome diaphragm coupled to the fluid path, and a first coupling element disposed to one side of the dome diaphragm; and a reusable component having a support, a pressure sensor permanently associated with the support, a reusable diaphragm in pressure communication with the sensor, and a second coupling element disposed to one side of the reusable diaphragm and providing a generally linear path which is generally parallel with the reusable diaphragm, the second coupling element receiving the first coupling element along the path, such that the dome diaphragm is brought into confronting relationship with the reusable diaphragm by sliding the first and second coupling elements into mating relationship along the generally linear path.

90. A medical pressure transducer comprising reusable component for use with a disposable dome having a fluid that adapted to be coupled to a patient, a dome diaphragm coupled to said fluid path, and a first coupling element disposed to one side of said dome diaphragm, the reusable component comprising:

a support;

a pressure sensor permanently associated with the support;

a reusable diaphragm in pressure communication with the sensor; and a second coupling element disposed to one side of the reusable diaphragm and providing a generally linear path which is generally parallel with the reusable diaphragm to receive said first coupling element, such that said dome diaphragm is brought into confronting relationship with the reusable diaphragm by sliding the first and second coupling elements into mating relationship along the generally linear path.

91. A medical pressure transducer comprising a disposable dome for use with a reusable component having a support, a pressure sensor permanently associated with said support, a reusable diaphragm in pressure communication with said sensor and first coupling element disposed to one side of said reusable diaphragm, the disposable dome comprising:

a body having an aperture defining a plane;

a fluid path adapted to be coupled to a patient, the fluid path extending into the body and communicating with the aperture;

a dome diaphragm coupled to the fluid path and extending across and sealing the aperture; and a generally linear coupling element disposed to one side of the dome diaphragm and extending generally in the plane defined by the aperture, the generally linear coupling element being shaped to slide along a generally linear path which is generally parallel with said reusable diaphragm into a coupled relationship with said first coupling element such that the dome diaphragm is brought into confronting relationship with said reusable diaphragm upon the coupling elements being matingly engaged in the coupled relationship by sliding the generally linear coupling element into the first coupling element in a direction which is generally linear and generally parallel to said reusable diaphragm.

92. A disposable medical pressure transducer dome for use with a reusable component having a support, a pressure sensor permanently associated with said support, a reusable diaphragm in pressure communication with said sensor, and a channel disposed adjacent said reusable diaphragm, said dome comprising:

A body having a plate-like backside to define a backside plane, the body having an aperture extendending therethrough;

A fluid path carried by the body and communicating with the aperture, the fluid path adapted to be coupled to a patient;

a dome diaphragm extending across the aperture; and the plate-like backside of the body having a wing extending outwardly from the body substantially in the backside plane, the wing being configured to be slidably received into said channel along a generally linear path which is generally parallel with said reusable diaphragm such that the dome diaphragm is moved into confronting relationship with said reusable diaphragm by sliding the wing in a direction which is generally linear and generally parallel to said reusable diaphragm.

* * * * *

UNITED STATES PATENT AND TRADEMARK OFFICE
CERTIFICATE OF CORRECTION

PATENT NO. : 5,752,918
DATED : May 19, 1998
INVENTOR(S) : Fowler et al

It is certified that error appears in the above-identified patent and that said Letters Patent is hereby corrected as shown below:

In the Abstract, line 11, change "with dome" to read --with the dome--;

Column 5, line 18, replace "comer" with --corner--;

Column 6, line 15, replace "180°" with --180--;

Column 7, line 32, change "tailing" to read --trailing--;

Column 11, line 34, change "434"" to read --434'--;

Column 11, line 42, change "434"" to read --434'--;

Column 11, line 46, change "434"" to read --434'--;

Column 15, line 49, change "comrpising" to read --comprising--.

UNITED STATES PATENT AND TRADEMARK OFFICE
CERTIFICATE OF CORRECTION

PATENT NO. : 5,752,918
DATED : May 19, 1998
INVENTOR(S) : Fowler et al

It is certified that error appears in the above-identified patent and that said Letters Patent is hereby corrected as shown below:

Column 17, lines 24-25, replace "component channel along a generally linear path which" with --diaphragm such that a dome diaphragm is brought into--;

Column 17, line 63, change "is pressure" to read --in pressure--;

Column 18, line 32, change "communication" to read --communicating--;

Column 18, line 60, change "communication" to read --communicating--;

Column 18, line 65, change "associate" to read --associated--;

Column 19, line 31, before "disposable dome" insert --a--;

Column 19, line 47, before "reusable" insert --a--;

Column 19, line 49, change "that adapted" to read --path adapted--; and

Column 20, line 43, change "extendending" to read --extending--.

Signed and Sealed this

Twenty-second Day of June, 1999

Attest:

Q. TODD DICKINSON

*Attesting Officer*   *Acting Commissioner of Patents and Trademarks*